United States Patent [19]

Takeshita et al.

[11] 4,299,771

[45] Nov. 10, 1981

[54] PROCESS FOR PRODUCING ANTHRAQUINONE COMPOUNDS

[75] Inventors: Akira Takeshita, Toyonaka; Kaneo Yokoyama, Nara; Makoto Hattori, Toyonaka, all of Japan

[73] Assignee: Sumitomo Chemical Company, Limited, Osaka, Japan

[21] Appl. No.: 197,625

[22] Filed: Oct. 16, 1980

[30] Foreign Application Priority Data

Oct. 26, 1979 [JP] Japan ................................. 51-138894
Nov. 29, 1979 [JP] Japan ................................. 54-155062

[51] Int. Cl.$^3$ ............................................. C07C 97/12
[52] U.S. Cl. ..................................................... 260/378
[58] Field of Search ................ 260/378, 465 E, 465 H

[56] References Cited

U.S. PATENT DOCUMENTS 3,203,751  8/1965  Hildreth ..................................... 8/39
4,042,605  8/1977  Hartwig .................................. 260/378

FOREIGN PATENT DOCUMENTS 935669  10/1955  Fed. Rep. of Germany .
1108704 12/1961  Fed. Rep. of Germany .
49-17643  5/1974  Japan .
1541497   3/1979  United Kingdom .
148066   6/1962  U.S.S.R. .

Primary Examiner—Winston A. Douglas
Assistant Examiner—Raymond K. Covington
Attorney, Agent, or Firm—Stevens, Davis, Miller & Mosher

[57] ABSTRACT

In a process for producing an anthraquinone dye intermediate, 1,4-diamino-2,3-dicyanoanthraquinone, by reacting 1,4-diaminoanthraquinone-2-sulfonic acid, a salt thereof, 1,4-diaminoanthraquinone-2-cyanoanthraquinone, 1,4-diamino-2,3-disulfonic acid, or a salt thereof with a cyanogenating agent in an aqueous medium, the yield and quality of the product can be improved markedly by carrying out the reaction in the presence of a quaternary ammonium compound, and further, depending upon the starting material used, in the presence or absence of a dehydrogenating agent.

15 Claims, No Drawings

PROCESS FOR PRODUCING ANTHRAQUINONE COMPOUNDS

The present invention relates to an improved process for producing an anthraquinone dye intermediate, more specifically, 1,4-diamino-2,3-dicyanoanthraquinone.

It is disclosed in German Pat. No. 536,998 and British Pat. No. 359,850 that 1,4-diamino-2,3-dicyanoanthraquinone can be obtained by reacting 1,4-diaminoanthraquinone-2-sulfonic acid in an aqueous solution with a cyano compound.

However, this process always gives as by-products 1,4-diamino-2-cyanoanthraquinone and 1,4-diaminoanthraquinone in definite amounts, so that the yield of the desired compound is as low as about 60% at best, and when used for the production of dyes, the product obtained is necessarily purified by use of a reagent, e.g., sulfuric acid.

As a method for preventing the formation of these by-products, it is disclosed to use an oxidizing agent, e.g., sodium m-nitrobenzenesulfonate in West German Pat. No. 1,108,704 and Soviet Pat. No. 148,066.

According to this method, it is sure that the formation of 1,4-diaminoanthraquinone is completely inhibited and the 1,4-diamino-2-cyanoanthraquinone content in the reaction product tends to decrease, but certain oxidation products and secondary by-products due to hydrolysis of the desired compound and by-products are formed to lower the purity, so that the resulting product cannot be used without purification for producing dyes giving brilliant blue shades, and moreover the yield is still as low as about 70-80%.

It is also disclosed in West German Pat. No. 935,669, U.S. Pat. No. 3,203,751, and Published Examined Japanese Patent Application No. 17643/1974 that 1,4-diamino-2,3-dicyanoanthraquinone is obtained by reacting 1,4-diaminoanthraquinone-2,3-disulfonic acid in an aqueous solution with a cyano compound. However, this known process yields as byproducts 1,4-diamino-2-cyanoanthraquinone-3-sulfonic acid and secondary products due to hydrolysis of the desired compound and by-products, and further the desired compound is inevitably contaminated with unreacted materials, so that the yield and purity are as low as about 90% and 86-88%, respectively, at the best. Consequently, in order to obtain dyes giving brilliant blue shades, the product obtained must be purified in a suitable manner.

The present inventors have earnestly studied a process for producing 1,4-diamino-2,3-dicyanoanthraquinone, and as a result found that the aforesaid drawbacks can be overcome by carrying out the reaction between 1,4-diaminoanthraquinone-2-sulfonic or 2,3-disulfonic acid or 1,4-diamino-2-cyanoanthraquinone with a cyanogenating agent in the presence of a quaternary ammonium compound.

Thus, the present invention provides a process for producing 1,4-diamino-2,3-dicyanoanthraquinone, which comprises reacting 1,4-diaminoanthraquinone-2-sulfonic acid or a salt thereof, 1,4-diamino-2-cyanoanthraquinone, or 1,4-diaminoanthraquinone-2,3-disulfonic acid or a salt thereof with a cyanogenating agent in an aqueous medium, in the presence or absence of a dehydrogenating agent, with use of a quaternary ammonium compound.

According to the process of the present invention, when the starting material is 1,4-diaminoanthraquinone-2-sulfonic acid, the 1,4-diamino-2-cyanoanthraquinone content, which inevitably reaches a level of 10-20% in the conventional processes, is lowered to 1-3% or less, and therefore the yield of the desired compound is markedly increased, and when the starting material is 1,4-diaminoanthraquinone-2,3-disulfonic acid, the total content of sulfonic acids such as 1,4-diamino-2-cyanoanthraquinone-3-sulfonic acid and the unreacted 1,4-diaminoanthraquinone-2,3-disulfonic acid, which inevitably reaches about 5-7% in the conventional processes, is lowered to 1-3% or less, and therefore the yield of the desired compound markedly increased. Of course, the desired compound is obtained in high yield, when the starting material is 1,4-diamino-2-cyanoanthraquinone.

Further, according to the process of this invention, the desired compound of high purity can be easily obtained merely by filtration of the reaction mixture after completion of the reaction, because almost all undesired organic compounds in the reaction mixture are dissolved in an aqueous medium. The quaternary ammonium compound can be fully recovered from the filtrate by use of an alkali, in the form of quaternary ammonium compound per se or hydroxide thereof, and the former can be reused as it is, and the latter can be also reused after extraction with an organic solvent, followed by back-extraction with an acid.

The process of the present invention is illustrated in detail as follows.

The quaternary ammonium compounds usable in this invention include lower alkyl quaternary ammonium compounds such as tetramethylammonium chloride, tetraethylammonium chloride, tetrabutylammonium chloride, tetramethylammonium methylsulfate, and tetraethylammonium ethylsulfate;

higher alkyl quaternary ammonium compounds such as lauryltrimethylammonium chloride, stearyltrimethylammonium chloride, and distearyl dimethylammonium chloride;

trialkylbenzylammonium compounds such as trimethylbenzylammonium chloride and triethylbenzylammonium chloride;

N-alkylpyridinium or N-alkylpicolinium compounds such as N-methylpyridinium chloride, N-ethylpyridinium chloride, N-butylpyridinium chloride, N-laurylpyridinium chloride, and N-stearylpyridinium chloride;

bromides, iodides, sulfates, phosphates, and acetates corresponding to the chlorides described above; and mixtures thereof.

Industrially preferred ones are the trialkylbenzylammonium compounds.

The amount of quaternary ammonium compound to be used varies depending upon the kind thereof and the starting materials, and is generally from 2 to 90% by weight based on the total weight of the quaternary ammonium compound and aqueous medium.

In the case of using lower alkyl quaternary ammonium compounds, it is from 30 to 80% by weight, preferably from 40 to 70% by weight, higher alkyl quaternary ammonium compounds, from 10 to 90% by weight, preferably from 15 to 80% by weight, trialkylbenzylammonium compounds, from 2 to 80% by weight, preferably from 2.5 to 70% by weight, N-alkylpyridinium or N-alkylpicolinium compounds, from 2 to 50% by weight, preferably from 5 to 40% by weight based on the total weight of the quaternary ammonium compound and aqueous medium. For example, in the case of using triethylbenzylammonium chloride, it is from 10 to 80% by weight, preferably 15 to 60% by weight based on the total weight of the quaternary ammonium compound and aqueous medium, when 1,4-diaminoanthraquinone-2-sulfonic acid or 1,4-diamino-2-cyanoanthraquinone is used as starting material, and is from 2 to 80% by weight, preferably 2.5 to 50% by weight based on the total weight of the quaternary ammonium compound and aqueous medium, when 1,4-diaminoanthraquinone-2,3-disulfonic acid is used as starting material. This amount may be smaller than the above value when the lipophilicity of the quaternary ammonium compound to be used is higher than that of triethylbenzylammonium chloride, and may be larger when the lipophilicity relationship is reversed, whereby desired results can be obtained.

The cyanogenating agents usable in this invention include ammonium cyanide or cyanides of alkali metals, or alkaline earth metals, e.g., sodium cyanide, potassium cyanide, magnesium cyanide, and calcium cyanide, and also include mixtures thereof. There may be also used cyanohydrins capable of generating cyano ion in water, such as acetone cyanohydrin. Of these, particularly preferred are sodium cyanide and potassium cyanide. The cyanogenating agent is used in an amount of 2.0 to 10 moles per mole of 1,4-diaminoanthraquinone-2-sulfonic acid or 1,4-diaminoanthraquinone-2,3-disulfonic acid and 1.0 to 5.0 moles per mole of 1,4-diamino-2-cyanoanthraquinone.

In this invention, when 1,4-diaminoanthraquinone-2-sulfonic acid or 1,4-diamino-2-cyanoanthraquinone is used as starting material, a dehydrogenating agent is added to the reaction system. The dehydrogenating agent includes for example, an organic nitro compound such as nitrobenzene, nitrobenzenesulfonic acid or nitrophenol; a sodium, potassium, or ammonium salt of an organic or inorganic peroxy acid such as peracetic acid, persulfuric acid, perboric acid, or perphosphoric acid; or sulfur. Moreover, oxygen-containing gas such as air is also usable. In this case, the reaction is carried out preferably in the presence of a catalyst such as ammonium molybdate or ammonium vanadate.

The amount of dehydrogenating agent to be used varies depending upon the kind thereof and is generally from 0.05 to 2.0 moles per mole of the starting material. For example, in the case of using sodium m-nitrobenzenesulfonate, it is from 0.1 to 1.6 moles, preferably 0.2 to 0.6 moles per mole of the starting material.

The reaction of this invention is carried out within the pH range preferably of 8-11, more preferably of 8.5-10.5. A pH lower than that is undesirable from the economical point of view, because liberation of hydrogen cyanide out of the reaction system easily occurs, while a pH higher than that is also undesirable because the hydrolysis of certain intermediates and the desired compound is promoted in the course of the reaction.

The pH value of the reaction mixture may be controlled, for example, by addition of a suitable amount of a usual buffering compound. It may also be controlled by adding a suitable acid, strong or weak, e.g., hydrochloric, sulfuric, phosphoric, formic, acetic or propionic acid, into the reaction mixture during cyanogenation.

The cyanogenation of this invention is carried out in an aqueous medium, which may contain a watermiscible organic solvent when a less soluble quaternary ammonium compound is used. Examples of said organic solvent include ethylene glycol, ethylene glycol monoalkyl ethers, diethylene glycol monoalkyl ethers, triethylene glycol, triethylene glycol monoalkyl ethers, formamide, methylformamide, dimethylformamide, N-alkylpyrrolidones, dimethylsulfoxide, sulfolane, hexamethylphosphoric acid triamide, methanol, ethanol, propanol, butanol, pyridine, picoline, and mixtures thereof.

The reaction temperature in this invention is about 40° to 100° C. More concretely speaking, it is 50° to 100° C., preferably 65° to 100° C., when the starting material is 1,4-diaminoanthraquinone-2-sulfonic acid or 1,4-diamino-2-cyanoanthraquinone, and it is 40° to 100° C., preferably 50° to 90° C., when the starting material is 1,4-diaminoanthraquinone-2,3-disulfonic acid. At a higher temperature within the above described ranges, the reaction tends to proceed rapidly, and therefore it is desirable to set the pH value as low as possible for preventing the hydrolysis. At a lower temperature, it is desirable to set the pH value as high as possible. A preferable procedure in accordance with the present invention is given as follows.

When the starting material is 1,4-diaminoanthraquinone-2-sulfonic acid or a salt thereof (sodium, potassium, ammonium salt or the like) or 1,4-diamino-2-cyanoanthraquinone, it is dissolved in a mixture of the quaternary ammonium compound and water, and if desired, the pH is adjusted to 7.0 by use of a hydroxide, carbonate, hydrogencarbonate, or acetate of an alkali or alkaline earth metal. Thereafter, the dehydrogenating agent is added thereto, and further if desired, a buffer may be added thereto. Subsequently, the cyanogenating agent is added thereto and cyanogenation is carried out within the pH and temperature ranges as described above.

When the starting materials is 1,4-diaminoanthraquinone-2,3-disulfonic acid or a salt thereof (sodium, potassium, ammonium salt or the like) it is dissolved in a mixture of the quaternary ammonium compound and water, and if desired, the pH is adjusted to 7.0 by use of a hydroxide, carbonate, hydrogencarbonate, or acetate of an alkali or alkaline earth metal. Further, if desired, a buffer may be added thereto. Subsequently, the cyanogenating agent is added thereto and cyanogenation is carried out within the pH and temperature ranges as described above.

In the above procedures, when the effect of buffer is unsatisfactory, a weak acid is added to the reaction system to neutralize hydroxide ions liberated as the reaction proceeds, thereby controlling the pH value within an optimum range. If desired, the cyanogenating agent may be continuously added dropwise to the reaction system while the reaction proceeds within the pH and temperature ranges as described above.

After the reaction has been completed, the excess cyanogenating agent is decomposed with sodium hypochlorite or hydrogen peroxide, and then the reaction mixture is filtered and washed with water, whereby the desired 1,4-diamino-2,3-dicyanoanthraquinone is obtained in high yield with high purity. The 1,4-diamino-2,3-dicyanoanthraquinone obtained in accordance with the present invention can be used without any purification as the intermediate for the production of dyes giving brilliant blue shades.

This invention is illustrated in more detail with reference to the following Examples. Unless otherwise noted, parts and % are by weight.

EXAMPLE 1

To a mixture of 360 parts of benzyltriethylammonium chloride with 840 parts of water, were added under stirring 110.0 parts of 1,4-diaminoanthraquinone-2-sulfonic acid of 90.9% purity and subsequently 30 parts of nitrobenzene. Stirring was continued at room temperature to complete dissolution.

Then, the pH was adjusted to 7.0 using 28% sodium hydroxide solution, and thereafter 382.1 parts of 25% sodium cyanide aqueous solution was added dropwise. While thoroughly stirring, the mixture was heated to 85°–90° C. to react until the starting material disappeared almost completely, which was confirmed by chromatography. During this reaction, the pH of the mixture was maintained within the range of 9.0–9.5 by use of 30% aqueous solution of sulfuric acid.

Then, excess sodium cyanide was decomposed with hypochlorous acid. Thereafter, by filtration, washing with hot water, and drying, 86.7 parts of a dark blue crystalline powder was obtained.

The yield based on 1,4-diaminoanthraquinone-2-sulfonic acid was determined, and the following results were obtained:

| | |
|---|---|
| 1,4-diamino-2,3-dicyanoanthraquinone | 90.5% |
| 1,4-diamino-2-cyanoanthraquinone | 1.6% |
| Unreacted starting material | 1.2% |

EXAMPLE 2

To a mixture of 400 parts of benzyltrimethylammonium chloride with 800 parts of water, were added under stirring 92.6 parts of 1,4-diamino-2-cyanoanthraquinone of 90% purity and subsequently 42.4 parts of sodium m-nitrobenzenesulfonate. Thereafter, 190.0 parts of 25% sodium cyanide aqueous solution was added dropwise. While thoroughly stirring, the mixture was heated to 80°–85° C. to react until the starting material disappeared almost completely, which was confirmed by chromatography. During this reaction, pH of the mixture was maintained within the range of 9.0–9.5 by use of a 30% aqueous solution of phosphoric acid. Then, excess sodium cyanide was decomposed with hydrogen peroxide. Thereafter, by filtration, washing with hot water, and drying, 95.6 parts of a dark blue crystalline powder was obtained.

The yield based on 1,4-diamino-2-cyanoanthraquinone was determined, and the following results were obtained:

| | |
|---|---|
| 1,4-diamino-2,3-dicyanoanthraquinone | 92.4% |
| Unreacted starting material | 2.1% |

EXAMPLE 3

To a mixture of 600 parts of lauryltrimethylammonium chloride with 400 parts of water, were added under stirring 110.0 parts of 1,4-diaminoanthraquinone-2-sulfonic acid of 90.9% purity and subsequently 30 parts of nitrobenzene. Stirring was continued at room temperature to complete dissolution. Then, the pH was adjusted to 7.0 using sodium carbonate, and thereafter 305.6 parts of 25% sodium cyanide aqueous solution was added dropwise. While thoroughly stirring, the mixture was heated to 80°–85° C. to react until the starting material disappeared almost completely, which was confirmed by chromatography. During this reaction, the pH of the mixture was maintained within the range of 9.0–9.5 by use of 30% aqueous solution of phosphoric acid.

After completion of the reaction, excess sodium cyanide was decomposed with hydrogen peroxide. Thereafter, by filtration, washing with hot water, and drying, 88.5 parts of a dark blue crystalline powder was obtained.

The yield based on 1,4-diaminoanthraquinone-2-sulfonic acid was determined, and the following results were obtained:

| | |
|---|---|
| 1,4-diamino-2,3-dicyanoanthraquinone | 92.2% |
| 1,4-diamino-2-cyanoanthraquinone | 1.3% |
| Unreacted starting material | 1.5% |

EXAMPLE 4

To a mixture of 60 parts of N-butylpyridinium chloride and 360 parts of pyridine with 780 parts of water, were added under stirring 110.0 parts of 1,4-diaminoanthraquinone-2-sulfonic acid of 90.9% purity and subsequently 35.0 parts of sodium m-nitrobenzenesulfonate. Stirring was continued at room temperature to complete dissolution.

Then, the pH was adjusted to 7.0 using 28% sodium hydroxide aqueous solution, and thereafter 310.0 parts of 25% potassium cyanide aqueous solution was added dropwise. While thoroughly stirring, the mixture was heated to 80°–85° C. to react until the starting material disappeared almost completely, which was confirmed by chromatography. During this reaction, the pH of the mixture was maintained within the range of 9.3–9.6 by use of 30% aqueous solution of sulfuric acid. Then, excess potassium cyanide was decomposed with hypochlorous acid. Thereafter, by filtration, washing with hot water, and drying, 88.9 parts of a dark blue crystalline powder was obtained.

The yield based on 1,4-diaminoanthraquinone-2-sulfonic acid was determined, and the following results were obtained:

| | |
|---|---|
| 1,4-diamino-2,3-dicyanoanthraquinone | 91.0% |
| 1,4-diamino-2-cyanoanthraquinone | 2.2% |
| Unreacted starting material | 1.4% |

EXAMPLE 5

To a mixture of 480 parts of benzyltriethylammonium chloride with 320 parts of water, were added under stirring 110.0 parts of 1,4-diaminoanthraquinone-2-sulfonic acid of 90.9% purity and subsequently 21.0 parts of nitrobenzene. Stirring was continued at room temperature to complete dissolution.

Then, the pH was adjusted to 7.0 using 28% sodium hydroxide aqueous solution, and thereafter 242.1 parts of 25% sodium cyanide aqueous solution was added dropwise. While thoroughly stirring, the mixture was heated to 75°–80° C. to react until the starting material disappeared almost completely, which was confirmed by chromatography. During this reaction, the pH of the mixture was maintained within the range of 9.0–9.5 by use of 30% aqueous solution of sulfuric acid. Then, excess sodium cyanide was decomposed with hydrogen peroxide. Thereafter, by filtration, washing with hot water, and drying, 87.0 parts of a dark blue crystalline powder was obtained.

The yield based on 1,4-diaminoanthraquinone-2-sulfonic acid was determined, and the following results were obtained:

| | |
|---|---|
| 1,4-diamino-2,3-dicyanoanthraquinone | 91.2% |
| 1,4-diamino-2-cyanoanthraquinone | 0.8% |
| Unreacted starting material | 1.4% |

EXAMPLE 6

To a mixture of 360 parts of benzyltriethylammonium chloride with 840 parts of water, was added 156.5 parts of 1,4-diaminoanthraquinone-2,3-disulfonic acid of 80.0% purity. Stirring was continued at room temperature to complete dissolution.

Then, the pH was adjusted to 7.0 using 28% sodium hydroxide aqueous solution, and thereafter 382.1 parts of 25% sodium cyanide aqueous solution was added dropwise. While thoroughly stirring, the mixture was heated to 70°–75° C. to react until the starting material disappeared almost completely, which was confirmed by chromatography. During this reaction, the pH of the mixture was maintained within the range of 9.0–9.5 by use of 30% aqueous solution of sulfuric acid.

Then, excess sodium cyanide was decomposed using hypochlorous acid. Thereafter, by filtration, washing with hot water, and drying, 88.7 parts of a dark blue crystalline powder was obtained.

The yield based on 1,4-diaminoanthraquinone-2,3-disulfonic acid was determined and the following results were obtained:

| | |
|---|---|
| 1,4-diamino-2,3-dicyanoanthraquinone | 96.0% |
| 1,4-diamino-2-cyanoanthraquinone-3-sulfonic acid and unreacted starting material | 2.0% |

The purity of the intended product was 97.0%, which is outstandingly high as compared with those obtained by the conventional processes.

EXAMPLE 7

To a mixture of 600 parts of lauryltrimethylammonium chloride with 400 parts of water, was added under stirring 156.5 parts of 1,4-diaminoanthraquinone-2,3-disulfonic acid of 80.0% purity. Stirring was continued at room temperature to complete dissolution. Then, the pH was adjusted to 7.0 using sodium carbonate, and thereafter 305.6 parts of 25% sodium cyanide aqueous solution was added dropwise. While thoroughly stirring, the mixture was heated to 65°–70° C. to react until the starting material disappeared almost completely, which was confirmed by chromatography. During this reaction, the pH of the mixture was maintained within the range of 9.0–9.5 by use of 30% aqueous solution of phosphoric acid.

After completion of the reaction, excess sodium cyanide was decomposed with hydrogen peroxide. Then, by filtration, washing with hot water, and drying, 89.9 parts of a dark blue crystalline powder was obtained.

The yield based on 1,4-diaminoanthraquinone-2,3-disulfonic acid was determined, and the following results were obtained:

| | |
|---|---|
| 1,4-diamino-2,3-dicyanoanthraquinone | 94.5% |
| 1,4-diamino-2-cyanoanthraquinone-3-sulfonic acid and unreacted starting material | 3.0% |

The purity of the intended product was 95.2%.

EXAMPLE 8

To a mixture of 60 parts of N-butylpyridinium chloride and 360 parts of pyridine with 780 parts of water, was added under stirring 156.5 parts of 1,4-diaminoanthraquinone-2,3-disulfonic acid of 80.0% purity. Then, the pH was adjusted to 7.0 by using 28% sodium hydroxide aqueous solution, and thereafter 310.0 parts of 25% potassium cyanide aqueous solution was added dropwise. While thoroughly stirring, the mixture was heated to 75°–80° C. to react until the starting material disappeared almost completely, which was confirmed by chromatography. During this reaction, the pH of the mixture was maintained within the range of 9.3–9.6 by use of 30% aqueous solution of sulfuric acid. Then, excess potassium cyanide was decomposed with hypochlorous acid. Thereafter, by filtration, washing with hot water, and drying, 91.5 parts of a dark blue crystalline powder was obtained.

The yield based on 1,4-diaminoanthraquinone-2,3-disulfonic acid was determined, and the following results were obtained:

| | |
|---|---|
| 1,4-diamino-2,3-dicyanoanthraquinone | 94.1% |
| 1,4-diamino-2-cyanoanthraquinone-3-sulfonic acid and unreacted starting material | 2.1% |

The purity of the intended product was 93.2%.

EXAMPLE 9

To a mixture of 480 parts of benzyltriethylammonium chloride with 320 parts of water, was added under stirring 156.5 parts of 1,4-diaminoanthraquinone-2,3-disulfonic acid of 80.0% purity. Stirring was continued at room temperature to complete dissolution.

Then, the pH was adjusted to 7.0 using 28% sodium hydroxide aqueous solution, and thereafter 242.1 parts of 25% sodium cyanide aqueous solution was added dropwise. While thoroughly stirring, the mixture was heated to 65°–70° C. to react until the starting material disappeared almost completely, which was confirmed by chromatography. During this reaction, the pH of the mixture was maintained within the range of 9.0–9.5 by use of 30% aqueous solution of sulfuric acid. Then, excess sodium cyanide was decomposed with hydrogen peroxide. Thereafter, by filtration, washing with hot water, and drying, 90.0 parts of a dark blue crystalline powder was obtained.

The yield based on 1,4-diaminoanthraquinone-2,3-disulfonic acid was determined, and the following results were obtained:

| | |
|---|---|
| 1,4-diamino-2,3-dicyanoanthraquinone | 96.7% |
| 1,4-diamino-2-cyanoanthraquinone-3-sulfonic acid and unreacted | | starting material 1.7%

The purity of the intended product was 97.3%.

EXAMPLE 10

To a mixture of 24 parts of benzyltriethylammonium chloride with 776 parts of water, was added under stirring 156.5 parts of 1,4-diaminoanthraquinone-2,3-disulfonic acid of 80.0% purity. Stirring was continued at room temperature to complete dissolution.

Then, the pH was adjusted to 7.0 using 28% sodium hydroxide aqueous solution, and thereafter 242.1 parts of 25% sodium cyanide aqueous solution was added dropwise. While thoroughly stirring, the mixture was heated to 70°–75° C. to react until the starting material disappeared almost completely, which was confirmed by chromatography. During this reaction, the pH of the mixture was maintained within the range of 9.4–10.0 by use of 50% sulfuric acid. Then, excess sodium cyanide was decomposed by hydrogen peroxide. Therafter, by filtration, washing with hot water, and drying, 90.0 parts of a dark blue crystalline powder was obtained.

The yield based on 1,4-diaminoanthraquinone-2,3-disulfonic acid was determined, and the following results were obtained:

| | |
|---|---|
| 1,4-diamino-2,3-dicyanoanthraquinone | 95.0% |
| 1,4-diamino-2-cyanoanthraquinone-3-sulfonic acid and unreacted starting material | 1.7% |

The purity of the intended product was 92.5%.

EXAMPLE 11

To a mixture of 600 parts of tetra-n-butyl-ammonium bromide with 600 parts of water, was added under stirring, 110.0 parts of 1,4-diaminoanthraquinone-2- sulfonic acid of 90.9% purity and subsequently 35.0 parts of sodium m-nitrobenzenesulfonate. Stirring was continued at room temperature to complete dissolution.

Then, the pH was adjusted to 7.0 using 28% sodium hydroxide solution, and thereafter 242.1 parts of 25% sodium cyanide aqueous solution was added dropwise. While thoroughly stirring, the mixture was heated to 80°–85° C. to react until the starting material disappeared almost completely, which was confirmed by chromatography. During this reaction, the pH of the mixture was maintained within the range of 9.4–9.8 by use of 30% aqueous solution of sulfuric acid. Then, excess sodium cyanide was decomposed with hydrogen peroxide. Therafter, by filtration, washing with hot water, and drying, 88.0 parts of a dark blue crystalline powder was obtained.

The yield based on 1,4-diaminoanthraquinone-2-sulfonic acid was determined, and the following results were obtained:

| | |
|---|---|
| 1,4-diamino-2,3-dicyanoanthraquinone | 90.0% |
| 1,4-diamino-2-cyanoanthraquinone | 2.3% |
| Unreacted starting material | 1.1% |

EXAMPLE 12

To a mixture of 600 parts of tetra-n-butylammonium bromide with 600 parts of water, was added under stirring, 156.5 parts of 1,4-diaminoanthraquinone-2,3-disulfonic acid of 80.0% purity. Stirring was continued at room temperature to complete dissolution.

Then, the pH was adjusted to 7.0 using 28% sodium hydroxide solution, and thereafter 242.1 parts of 25% sodium cyanide aqueous solution was added dropwise. While thoroughly stirring, the mixture was heated to 65°–70° C. to react until the starting material disappeared almost completely, which was confirmed by chromatography. During this reaction, the pH of the mixture was maintained within the range of 9.4–9.8 by use of 30% aqueous solution of sulfuric acid. Then, excess sodium cyanide was decomposed with hydrogen peroxide. Thereafter, by filtration, washing with hot water; and drying, 89.4 parts of a dark blue crystalline powder was obtained.

The yield based on 1,4-diaminoanthraquinone-2,3-disulfonic acid was determined, and the following results were obtained:

| | |
|---|---|
| 1,4-diamino-2,3-dicyanoanthraquinone | 96.0% |
| 1,4-diamino-2-cyanoanthraquinone-3-sulfonic acid and unreacted starting material | 1.7% |

The purity of the intended product was 97.3%.

REFERENTIAL EXAMPLE 1

(Example of absence of quaternary ammonium compound)

To 1200 parts of water, were added under stirring 110.0 parts of the same 1,4-diaminoanthraquinone-2-sulfonic acid as used in Example 1 and subsequently 30 parts of nitrobenzene. Stirring was continued at room temperature to complete dissolution.

Then, the pH was adjusted to 7.0 using 28% sodium hydroxide aqueous solution, and thereafter 382.1 parts of 25% sodium cyanide aqueous solution was added dropwise. While thoroughly stirring, the mixture was heated to 85°–90° C. to react until starting material disappeared almost completely, which was confirmed by chromatography. During this reaction, the pH of the mixture was maintained within the range of 9.0–9.5 by use of 30% aqueous solution of sulfuric acid.

Then, excess sodium cyanide was decomposed by hypochlorous acid. Thereafter, by filtration, washing with hot water, and drying, 92.5 parts of a dark blue crystalline powder was obtained.

The yield based on 1,4-diaminoanthraquinone-2-sulfonic acid was determined, and the following results were obtained:

| | |
|---|---|
| 1,4-diamino-2,3-dicyanoanthraquinone | 74.3% |
| 1,4-diamino-2-cyanoanthraquinone | 15.2% |
| Unreacted starting material | 3.7% |

REFERENTIAL EXAMPLE 2

(Example of absence of quaternary ammonium salt)

To 1200 parts of water, was added under stirring 156.5 parts of the same 1,4-diaminoanthraquinone-2,3-disulfonic acid as used in Example 6. Stirring was continued at room temperature to complete dissolution.

Then, the pH was adjusted to 7.0 by using 28% sodium hydroxide aqueous solution, and thereafter 382.1 parts of 25% sodium cyanide aqueous solution was added dropwise. While thoroughly stirring, the mixture was heated to 70°–75° C. to react until the starting material disappeared almost completely, which was confirmed by chromatography. During this reaction, the pH of the mixture was maintained within the range of 9.0–9.5 by use of 30% sulfuric acid aqueous solution. Then, excess sodium cyanide was decomposed by hypochlorous acid. Thereafter, by filtration, washing with hot water, and drying, 95.3 parts of a dark blue crystalline powder was obtained.

The yield based on 1,4-diaminoanthraquinone-2,3-disulfonic acid was determined, and the following results were obtained:

| | |
|---|---|
| 1,4-diamino-2,3-dicyanoathra-quinone | 91.5% |
| 1,4-diamino-2-cyanoanthraquinone-3-sulfonic acid and unreacted starting material | 5.0% |

The purity of the intended product was 87.0%, and no results better in product quality or yield than these results could not be obtained, although the reaction was repeated by varying reaction conditions.

What is claimed is:

1. A process for producing 1,4-diamino-2,3-dicyanoanthraquinone, which comprises reacting 1,4-diaminoanthraquinone-2-sulfonic acid or a salt thereof, 1,4-diamino-2-cyanoanthraquinone, or 1,4-diaminoanthraquinone-2,3-disulfonic acid or a salt thereof with a cyanogenating agent in an aqueous medium, in the presence or absence of a dehydrogenating agent, with use of a quaternary ammonium compound.

2. A process according to claim 1, wherein the reaction is carried out using 1,4-diaminoanthraquinone-2-sulfonic acid or a salt thereof, or 1,4-diamino-2-cyanoanthraquinone in the presence of a dehydrogenating agent.

3. A process according to claim 1, wherein the reaction is carried out using 1,4-diaminoanthraquinone-2,3-disulfonic acid or a salt thereof in the absence of a dehydrogenating agent.

4. A process according to claim 1, wherein the quaternary ammonium compound is at least one member selected from the group consisting of lower alkyl quaternary ammonium compounds, higher alkyl quaternary ammonium compounds, trialkylbenzylammonium compounds, N-alkylpyridinium compounds, and N-alkylpicolinium compounds.

5. A process according to claim 1, wherein the quaternary ammonium compound is at least one trialkylbenzylammonium compound.

6. A process according to claim 1, wherein the amount of said quaternary ammonium compound used is 2–90% by weight based on the total weight of the quaternary ammonium compound and aqueous medium.

7. A process according to claim 5, wherein the amount of said trialkylbenzylammonium compound used is from 2 to 80% by weight based on the total weight of quaternary ammonium compound and aqueous medium.

8. A process according to claim 4, wherein the amount of said lower alkyl quaternary ammonium compound used is from 30 to 80% by weight based on the total weight of quaternary ammonium compound and aqueous medium.

9. A process according to claim 4, wherein the amount of said higher alkyl quaternary ammonium compound used is from 10 to 90% by weight based on the total weight of quarternary ammonium compound and aqueous medium.

10. A process according to claim 4, wherein the amount of said N-alkylpyridinium compound or N-alkylpicolinium compound used is from 2 to 50% by weight based on the total weight of quaternary ammonium compound and aqueous medium.

11. A process according to claim 1, wherein the cyanogenating agent is sodium cyanide, potassium cyanide, ammonium cyanide, magnesium cyanide, calcium cyanide or acetone cyanohydrin.

12. A process according to claim 1, wherein the reaction is carried out at a temperature of about 40°–100° C.

13. A process according to claim 1, wherein the reaction is carried out within the pH range of 8–11.

14. A process according to claim 1, wherein the cyanogenating agent is used in an amount of 1.0 to 5.0 moles per mole of 1,4-diamino-2-cyanoanthraquinone.

15. A process according to claim 1, wherein the cyanogenating agent is used in an amount of 2.0 to 10 moles per mole of 1,4-diaminoanthraquinone-2-sulfonic acid or 1,4-diaminoanthraquinone-2,3-disulfonic acid.

* * * * *